(12) United States Patent
Suzuki

(10) Patent No.: US 7,029,545 B2
(45) Date of Patent: Apr. 18, 2006

(54) PROCESS FOR MAKING A DISPOSABLE WEARING ARTICLE

(75) Inventor: Seiji Suzuki, Kagawa-ken (JP)

(73) Assignee: Uni-Charm Corporation, Ehime-ken (JP)

( * ) Notice: Subject to any disclaimer, the term of this patent is extended or adjusted under 35 U.S.C. 154(b) by 330 days.

(21) Appl. No.: 10/083,296

(22) Filed: Feb. 27, 2002

(65) Prior Publication Data

US 2002/0148550 A1    Oct. 17, 2002

(30) Foreign Application Priority Data

Feb. 28, 2001  (JP)  .............................. 2001-054305
Sep. 26, 2001  (JP)  .............................. 2001-293342

(51) Int. Cl.
  *B32B 31/00*    (2006.01)
  *A61F 13/15*    (2006.01)

(52) U.S. Cl. ...................... 156/160; 156/163; 156/164; 156/290; 156/291; 156/295; 427/175; 427/207.1; 427/256

(58) Field of Classification Search ................ 156/161, 156/163, 164, 290, 291, 295; 427/175, 207.1, 427/208.2, 210, 256, 427
See application file for complete search history.

(56) References Cited

U.S. PATENT DOCUMENTS 6,077,375 A *  6/2000  Kwok ........................ 156/161
6,200,635 B1 *  3/2001  Kwok ........................ 427/286
6,235,137 B1 *  5/2001  Van Eperen et al. ........ 156/176

FOREIGN PATENT DOCUMENTS

| EP | 0 950 436 A | 10/1999 |
| WO | WO 00/66351 A | 11/2000 |
| WO | WO 01/76772 A | 10/2001 |
| WO | WO 03/051256 A | 6/2003 |

* cited by examiner

Primary Examiner—Jeff H. Aftergut
Assistant Examiner—Justin Fischer
(74) Attorney, Agent, or Firm—Clark & Brody

(57) ABSTRACT

A process for making a disposable wearing article for securing an elastic member to the wearing article without reducing a comfortable feeling of touch with a wearer's skin of the wearing article. A production line of the wearing article includes a step of securing elastic member to a sheet material using an adhesive. The elastic member is coated on its peripheral surface with the adhesive in a pattern of substantially continuous line and then the elastic member secured to sheet material of the wearing article. The continuous line runs in a longitudinal direction of the elastic member so that the curved line undulates on a plane defined by developing the peripheral surface of the elastic member with a height of undulation substantially corresponding to or being larger than a circumferential length A of the elastic member.

3 Claims, 7 Drawing Sheets

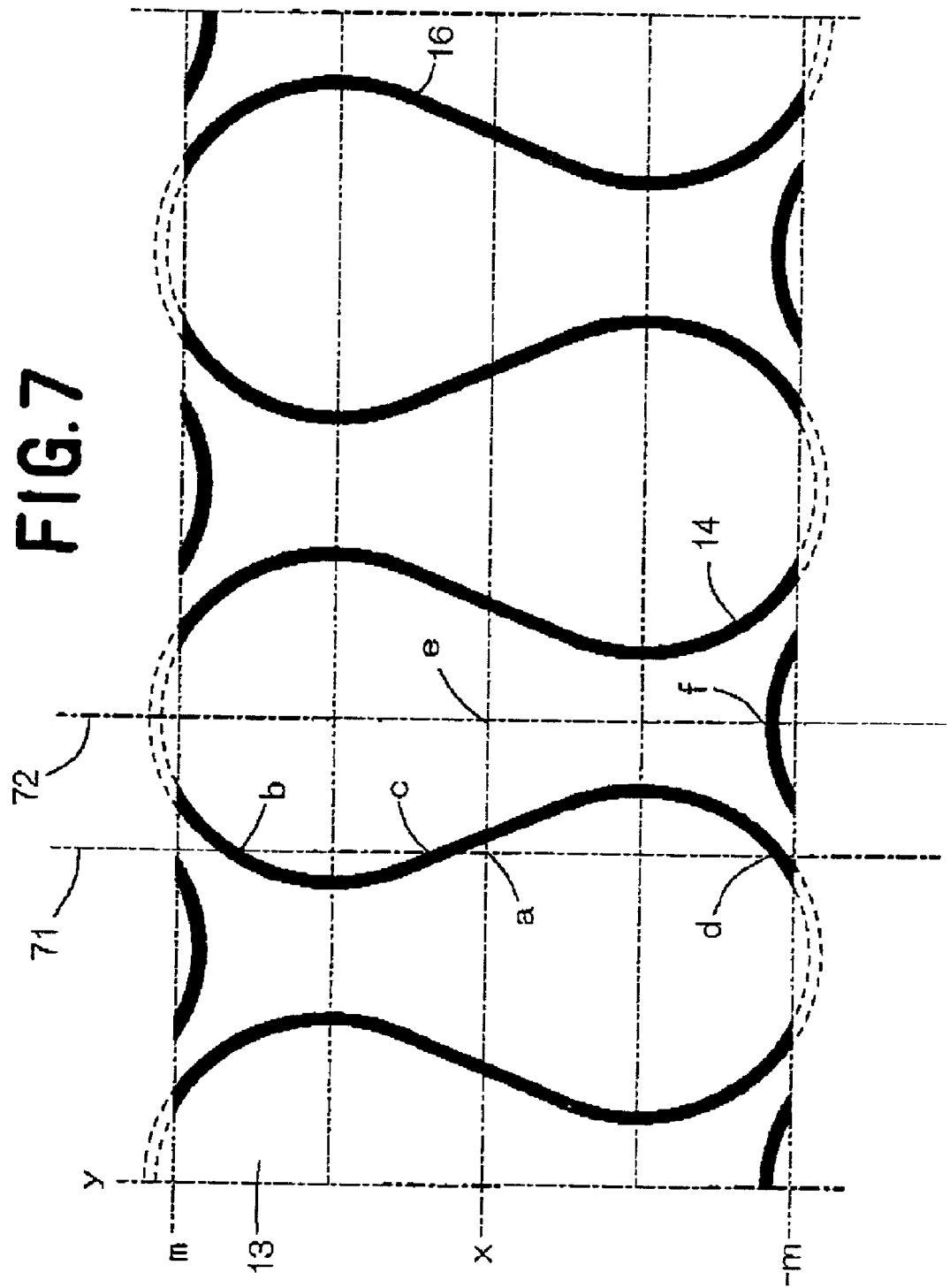

PROCESS FOR MAKING A DISPOSABLE WEARING ARTICLE

BACKGROUND OF THE INVENTION

This invention relates to a process for making a wearing article destined to be thrown away after a single use such as a disposable diaper and this process to make the wearing article includes a step of bonding an elastically stretchable string-like member to such wearing article.

Conventionally, securing of a string-like member such as rubber strings to a wearing article of this type has often been achieved using an appropriate adhesive. In general, a sheet material such as nonwoven fabric forming the wearing article has been coated on its surface with the adhesive over a desired width or the thread-like member has been coated on its surface with the adhesive intermittently in a longitudinal or a circumferential direction.

In the background of the former art, the width over which the sheet material is coated with an adhesive is preferably as narrow as possible in order to avoid an anxiety that a flexibility of the sheet material might be reduced by a cured adhesive. However, on the production line along which both the sheet material and the elastically stretchable string-like member are fed into the machine generally at such a high speed as to make it difficult to accurately control the position of these sheet material and elastically stretchable member, reduction of the width over which the sheet material should be coated with the adhesive is inevitably limited. In other words, this process is always accompanied by the problem that the flexibility of the sheet material may be reduced over a width substantially larger than the width of the string-like member itself. Such problem is particularly serious in the wearing article using a plurality of string-like members extending in parallel one to another.

In the latter case in which the string-like member is coated with the adhesive intermittently in its longitudinal direction, the adhesive applied surface of the string-like member may not properly face the sheet material to which the thread-like member should be bonded so far as the string-like member is running and oscillating at a high speed. Thus it is difficult to reliably bond the string-like member to the sheet material.

SUMMARY OF THE INVENTION

It is an object of this invention to improve the conventional process for making a disposable wearing article so that an elastic member of an elastically stretchability in its longitudinal direction can be reliably secured to a sheet material constituting a disposable wearing article without an anxiety that a comfortable feeling of touch with a wearer's skin of the disposable wearing article might be reduced due to the coating of the elastic member with an adhesive over a relatively large region in width.

According to this invention, there is provided a process for making a disposable wearing article including a step of bonding an elastic member of an elastically stretchability in a longitudinal direction to a disposable wearing article using an adhesive.

The step of securing the elastic member to the article includes a step of applying the adhesive to the elastic member on its peripheral surface in such a manner as to make the adhesive draw substantially a continuous line and then securing the elastic member to the sheet material; the continuous line draws a curved line on the x-y plane defined by a x-axis extending in the longitudinal direction and a y-axis of being orthogonal to the x-axis and corresponding to a developed view of the peripheral surface of the elastic member so that the curved line advances in the direction of the x-axis so as to undulate about the x-axis in the direction or the y-axis; and a height of the undulation is substantially equal to or larger than a circumferential length of the elastic member.

This invention may include in other preferred manners as follow:

(1) The curved line undulates, as viewed in the developed view, substantially with a uniform cycle and an amplitude in at least a partial section of the curved line in the direction of the x-axis.
(2) The elastic member is secured with or without extension to the sheet material.
(3) The curved line includes, as viewed in the developed view, sections curved in a S-shape or an inverted S-shape.
(4) The wearing article is any one of a disposable diaper, disposable training pants, a sanitary napkin, a disposable gown and disposable trousers.

BRIEF DESCRIPTION OF THE DRAWINGS

FIG. 7 is a view similar to FIG. 3 but showing additional embodiment of this invention.

DETAILED DESCRIPTION OF THE PREFERRED EMBODIMENTS

A process according to this invention for making a disposable wearing article will be more fully understood from the description given hereunder in reference to the accompanying drawings.

Figure 1:
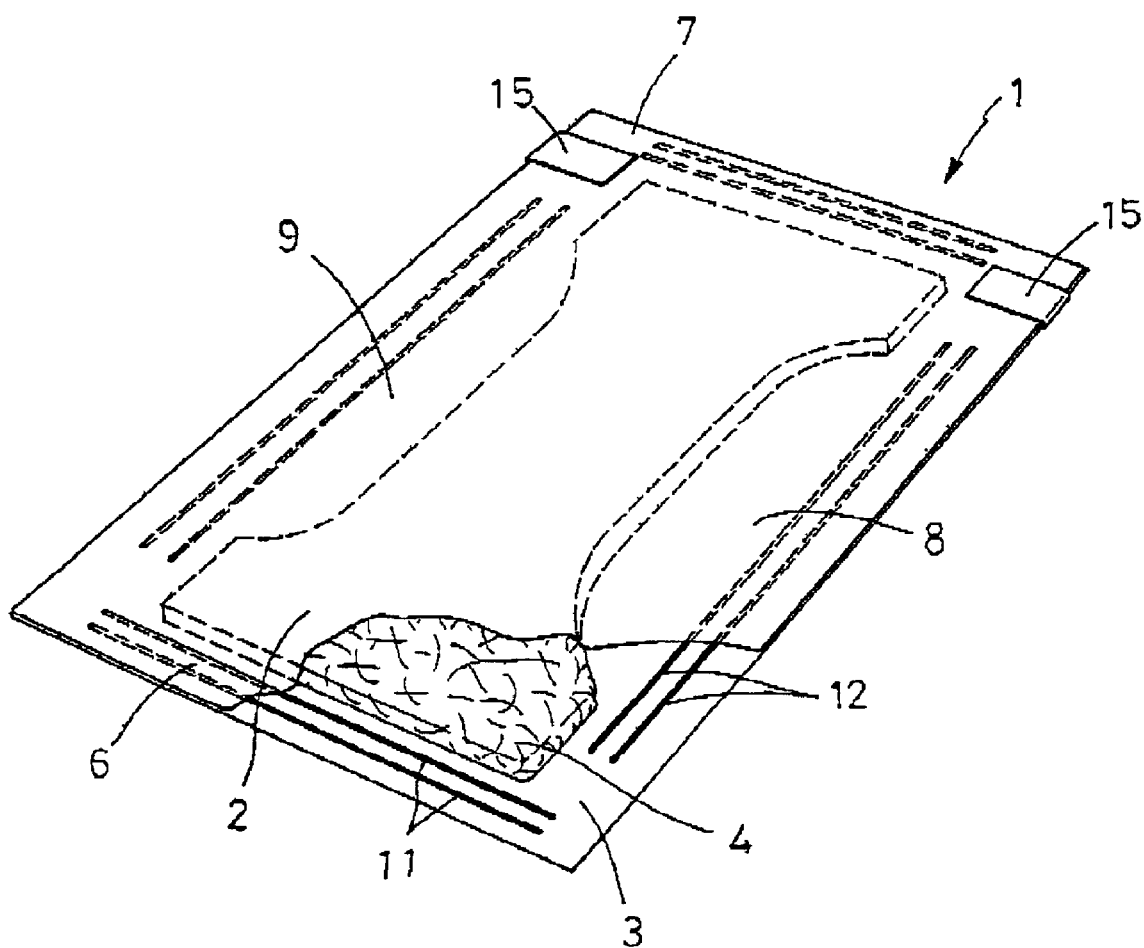
FIG. 1 is a partially cut away perspective view showing a disposable diaper.

FIG. 1 is a partially cut away perspective view showing a disposable diaper 1 obtained using the process according to this invention. The diaper 1 is a typical disposable wearing article relating to this invention and comprises a liquid-pervious topsheet 2, a liquid-impervious backsheet 3 and a liquid-absorbent core 4 disposed between these two sheets 2, 3. The top- and backsheets 2, 3 extend outwardly beyond a peripheral edge of the core 4 and are placed upon and joined to each other in respective extensions thereof so as to form front and rear end flaps 6, 7 and a pair of side flaps 8, 9. In the front and rear end flaps 6, 7, elastic members 11 in a form of plural thread-like elastic elements or ribbon-like elastic members or strand-like elastic members respectively extend in a transverse direction of the diaper 1 and are attached under extension between the top- and backsheets 2, 3 so as to be associated with a waist-hole. In the side flaps 8, 9, on the other hand, a plurality of elastic members 12 destined to be associated with respective leg-holes extend in a longitudinal direction of the diaper 1 and are attached under extension between the top- and backsheets 2, 3. In the vicinity of the end flap 7, the side flaps 8, 9 are provided with tape fasteners 15, respectively.

Figure 2:
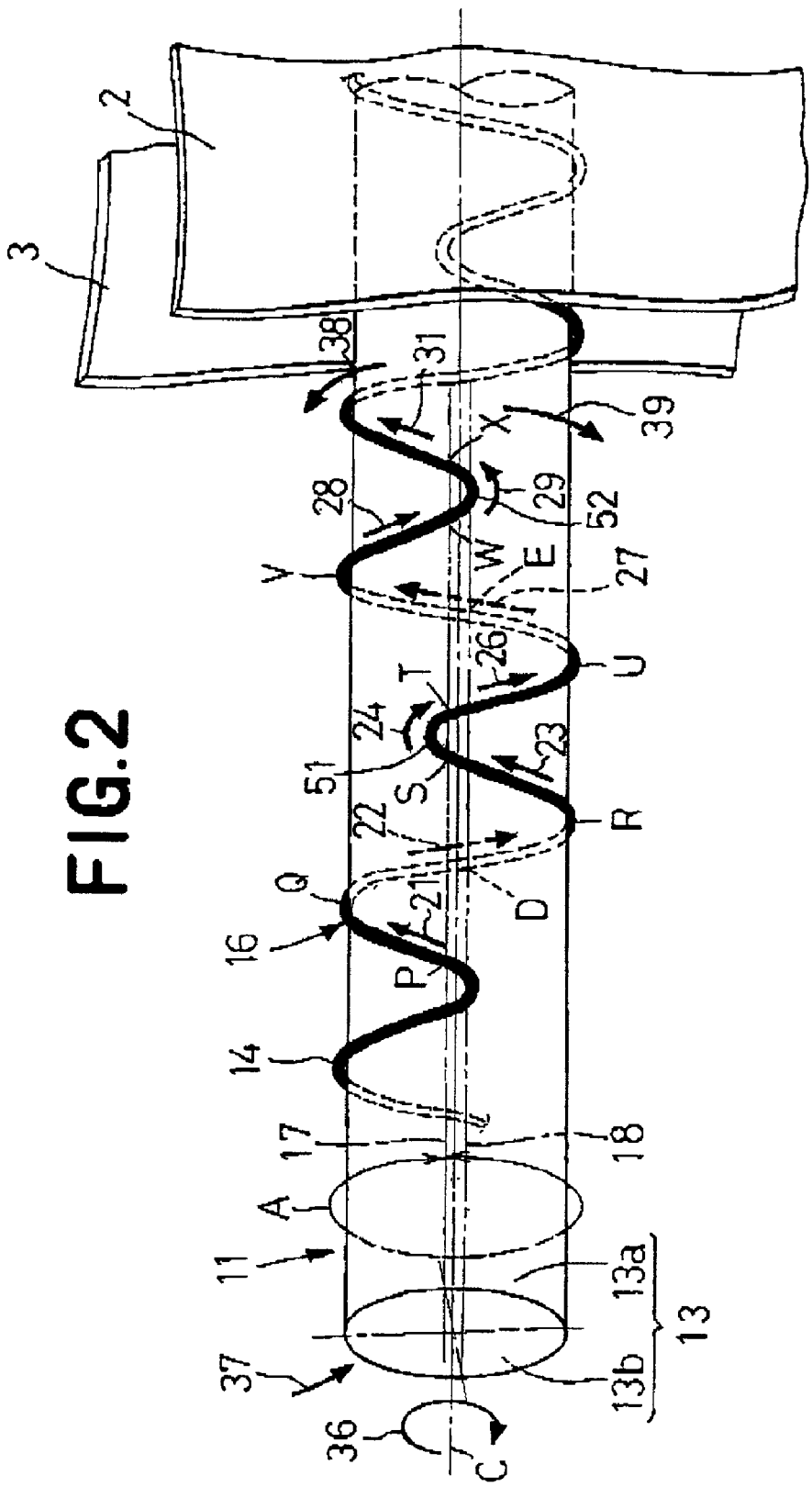
FIG. 2 is a fragmentary perspective view showing an elastic member and top- and backsheets.

FIG. 2 is a fragmentary perspective view illustrating one of the elastic members 11 associated with the waist-hole together with the top- and backsheets 2, 3 to which this elastic member 11 should be secured. The elastic member 11 is substantially a string-like member with a circular cross-section and has a circumferential length A and a longitudinal axis C in the direction of which the member 11 is elastically stretchable. An adhesive 14 is applied to the elastic member 11 on its peripheral surface 13 along the longitudinal axis C in a pattern of a continuous curved line 16 as illustrated.

Referring to FIG. 2, a manner of the curved line 16 advancing from the left to the right side of the axis C is described below. The peripheral surface 13 consists of a front half portion 13a and a rear half portion 13b. A first imaginary line 17 is drawn on the front half portion 13a in parallel to the longitudinal axis C so as to bisect vertically the front half portion 13a and intersect the curved line 16 at points P, S, T, W, X. A second imaginary line 18 is drawn on the rear half 13b in parallel to the longitudinal axis C so as to bisect vertically the rear half portion 13b and intersect the curved line 16 at points D, E. The curved line 16 advancing generally rightward from the point P following the direction of an allow 21 reaches the point Q approximately ¼ turn of the peripheral surface of the elastic member 11. Then the curved line 16 advances to the rear half following the direction of an arrow 22 to the point D from which the curved line 16 further goes around approximately ½ turn of the peripheral surface of the elastic member 11 until reaching the point R. Now the curved line 16 comes again on the front half portion 13a in the direction of an arrow 23 so as to go around approximately ¼ turn of the peripheral surface of the elastic member 11 till the point S. In this manner, the curved line 16 fully turns around the elastic member 11 on its peripheral surface between the point P and the point S. The curved line 16 further advances from the point S in the direction of an arrow 24 beyond the imaginary line 17 and then reverses its course to the point T. The curved line 16 continues to advance from the point T in the directions of arrows 26, 27, 28 in this order, passing the points U, E, V to the point W. In this manner, the curved line 16 fully runs again around the elastic member 11 on its peripheral surface. From the point W, the curved line 16 advances in the direction of an arrow 29 to the point X. The curved line 16 running from the point X in the direction of an arrow 31 draws the same locus as drawn by the curved line 16 starting from the point P. In other words, one cycle of the curved line 16 is defined by the distance from the point P to the point X. The elastic member 11 around the peripheral surface of which such curved line 16 is drawn by the applied adhesive 14 is fed under extension to desired regions on the inner surfaces of the top- and backsheets 2, 3 so as to be secured to these regions. In this process, the elastic member 11 comes in line-contact with the top- and backsheets 2, 3 along the first imaginary line 17 and the second imaginary line 18, respectively, so that the elastic member 11 is secured to the topsheet 2 at the points P, S, T, W, X . . . and to the backsheet 3 at the points D, E . . . Even if the elastic member 11 is rotated or twisted around its longitudinal axis C to the direction of an arrow 36 or to its reverse direction when the member 11 is being fed to the top- and backsheets 2, 3, the elastic member 11 is reliably bonded to the top- and backsheets 2, 3 if the line along which the peripheral surface 13 of the elastic member 11 comes in line-contact with the top- and backsheets 2, 3, respectively. Because there are definitely spots on the line coated with the adhesive 14 at appropriate intervals. After bonded to the top- and backsheets 2, 3, a contraction of the elastic member 11 on the topsheet 2 serves to form gathers between the points P and S, S and T, T and W, and W and X, respectively, and causes the backsheet 3 to form gathers between the points D and E.

Figure 3:
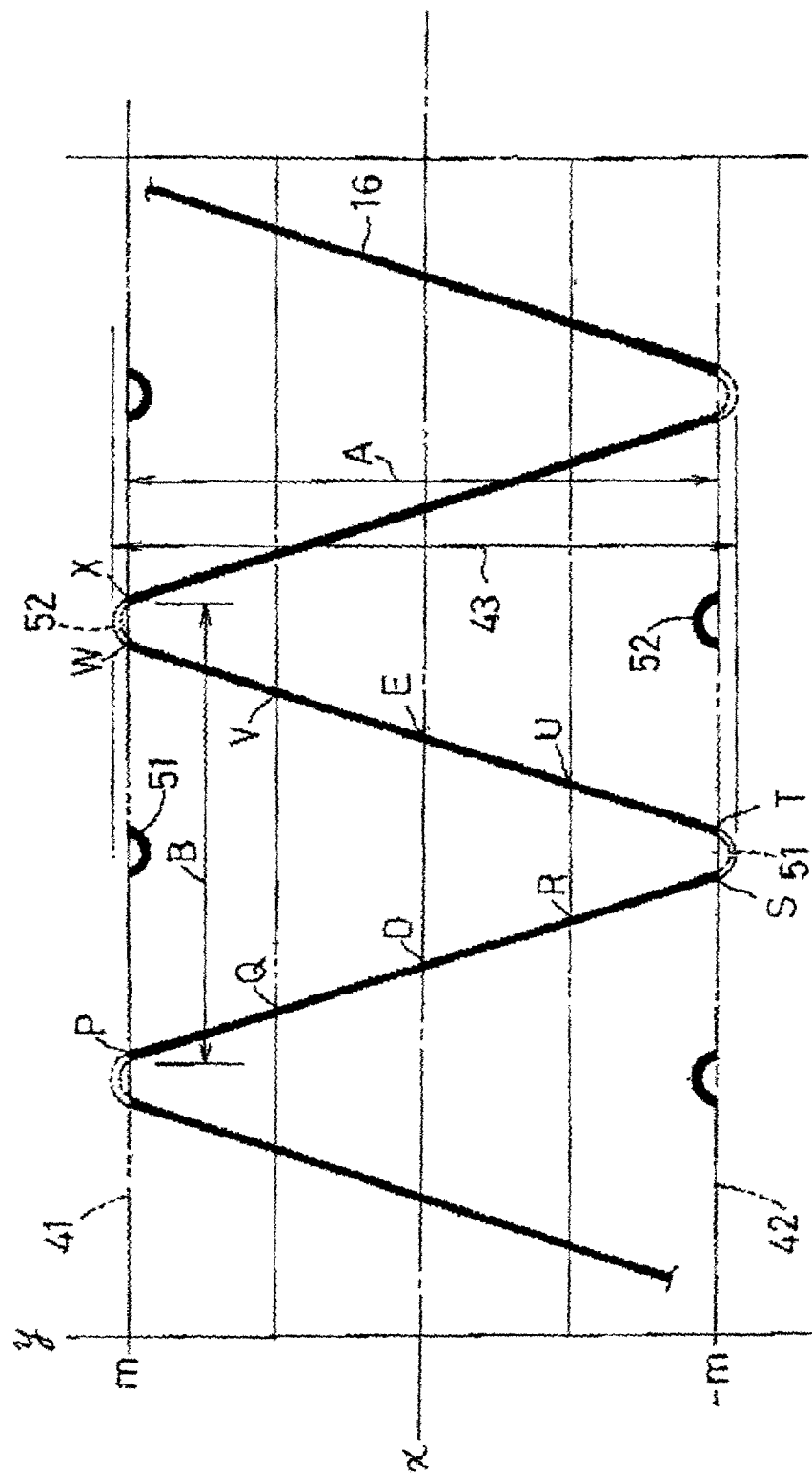
FIG. 3 is a diagram illustrating a peripheral surface of the elastic member as developed in a planar state.

FIG. 3 is a developed view illustrating the peripheral surface 13 of the elastic member 11 shown in FIG. 2 as has been developed in a planar state. This developed view illustrates the peripheral surface 13 as viewed in the direction indicated by an arrow 37 in FIG. 2, i.e., from the side of the rear half portion 13b. Referring to FIG. 3, an x-axis in FIG. 3 extends in parallel to the longitudinal axis C of the elastic member 11 and coincides with the second imaginary line 18 in FIG. 2. A y-axis is orthogonal to the x-axis and x-y plane including these x- and y-axes corresponds to the plane defined by the developed peripheral surface 13 and therefore coincides with the plane of FIG. 3. More specifically, the front half portion 13a of the peripheral surf ace 13 is vertically bisected along a cut-line coinciding with the first imaginary line 17 so that a curved upper half of the front half portion 13a is developed to the direction of an arrow 38 and a curved lower half is developed in the direction of an arrow 39 as shown in FIG. 2. Values indicated on the y-axis represent circumferential dimensions of the elastic member 11 with reference to the x-axis and lines 41, 42 extending in parallel to the x-axis: and passing through m and –m on the y-axis correspond to the first imaginary line 17 in FIG. 2. In other words, distances from the x-axis to m and –m are respectively equal to ½ of the circumferential length A of the elastic member 11.

In FIG. 3, the points in FIG. 2 corresponding to the points P–X, D, E are designated by the same letters. In order that the entire shape of the continuous curved line 16 way be easily understood, a section 51 of the curved line 16 extending between the points S and T and a section 52 of the curved line 16 between the points W and X in FIG. 2 are illustrated in FIG. 3 as an imaginary line section 51 underlying the straight line 42 passing through –m and an imaginary line section 52 overlying the straight line 41 passing through m. The curved line 16 described on the x-y plane in FIG. 3 vertically undulates about the x-axis like sine curve and a height 43 of such undulation, ie., amplitude of the curved line 16 is larger than the circumferential length A of the elastic member 11. Such curved line 16 forms a continuous line extending around the full circumference of the elastic member 11.

Figure 4:
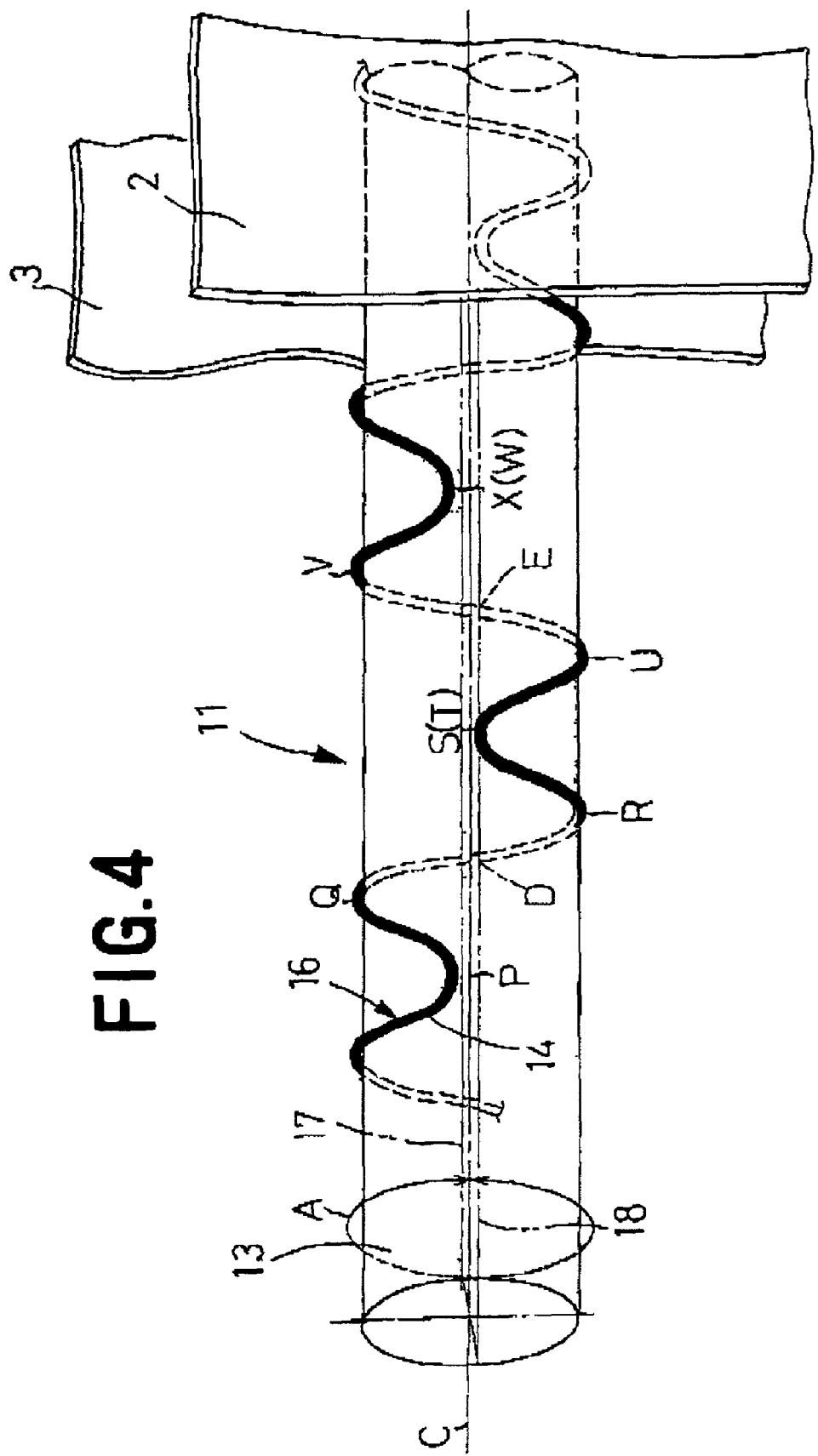
FIG. 4 is a view similar to FIG. 2 but showing another embodiment of this invention.

FIG. 4 is a view similar to FIG. 2 but showing one preferred embodiment of this invention. According to this embodiment, the curved line 16 drawn by the adhesive 14 comes substantially in contact with the first imaginary line 17 on the elastic member 11 rather than intersecting the first imaginary line 17. This means that the undulation height 43 of the curved line 16 approximately corresponds to the circumferential length A of the elastic member 11. In this case also, the applied adhesive 14 forms the curved line 16 substantially running around the entire circumference of the elastic member 11. Assumed that the elastic member 11 should be secured to the top- and backsheets 2, 3 both made of a flexible sheet material such as nonwoven fabric or plastic film, the elastic member 11 will come in contact with such sheet material along the first and second imaginary lines 17, 18 not over an extremely restricted region in width but over a relatively large region in width about these imaginary lines 17, 18, With a consequence, the object of this invention can be achieved even through the curved line 16 substantially comes in contact with the first imaginary line 17 as seen in FIG. 4 rather than intersecting this first imaginary line 17.

Figure 5:
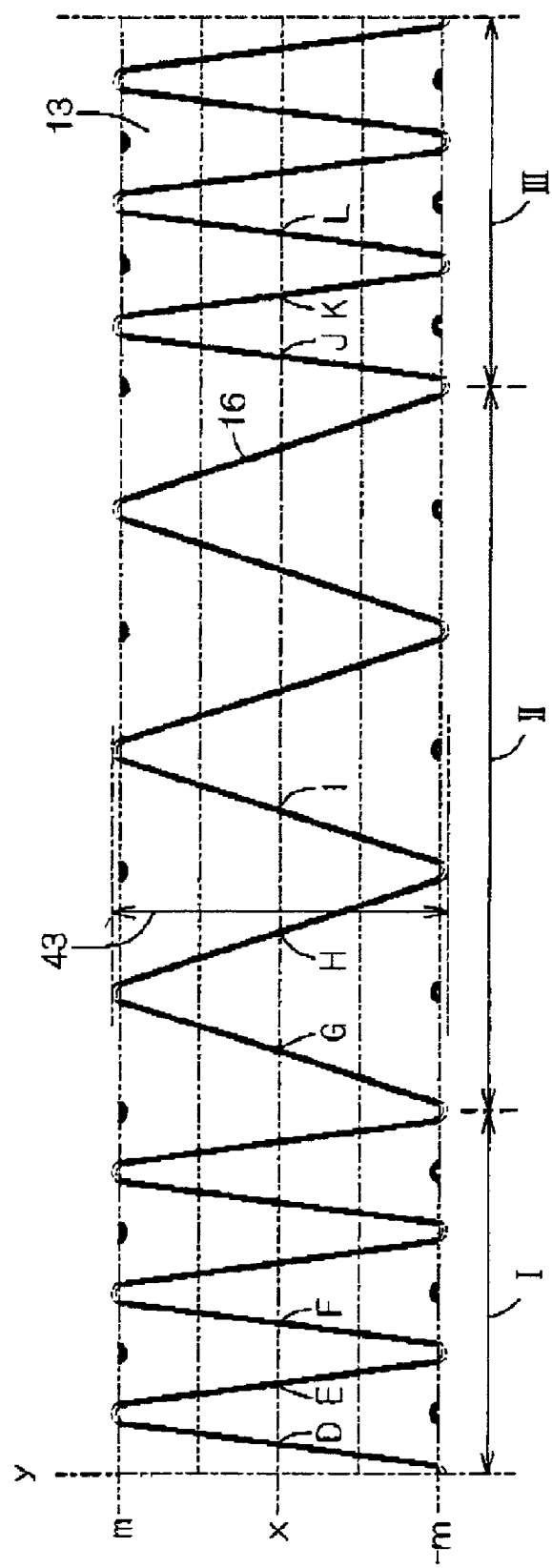
FIG. 5 is a view similar to FIG. 3 but showing still another embodiment of this invention.

FIG. 5 is a view similar to FIG. 3 but showing still another embodiment of this invention. The curved line 16 illustrated on the peripheral surface 13 developed here in the x-y plane undulates like sine curve having a uniform undulation height 43 and runs in the direction of the x-axis similarly to the case illustrated by FIG. 3. The curved line 16 in FIG. 5 is distinguished from that illustrated by FIG. 3 in that the cycle of the undulation depends on the sections along the x-axis. More specifically, the length of a cycle D-F in the section I is relatively short, the length of a cycle G-I in the section II is relatively long and the length of a cycle J-L in the section III is again reduced to the length of the cycle D-F. As in this embodiment, the curved line 16 may have an undulating cycle varying in the length in appropriate sections along the x-axis.

Figure 6:
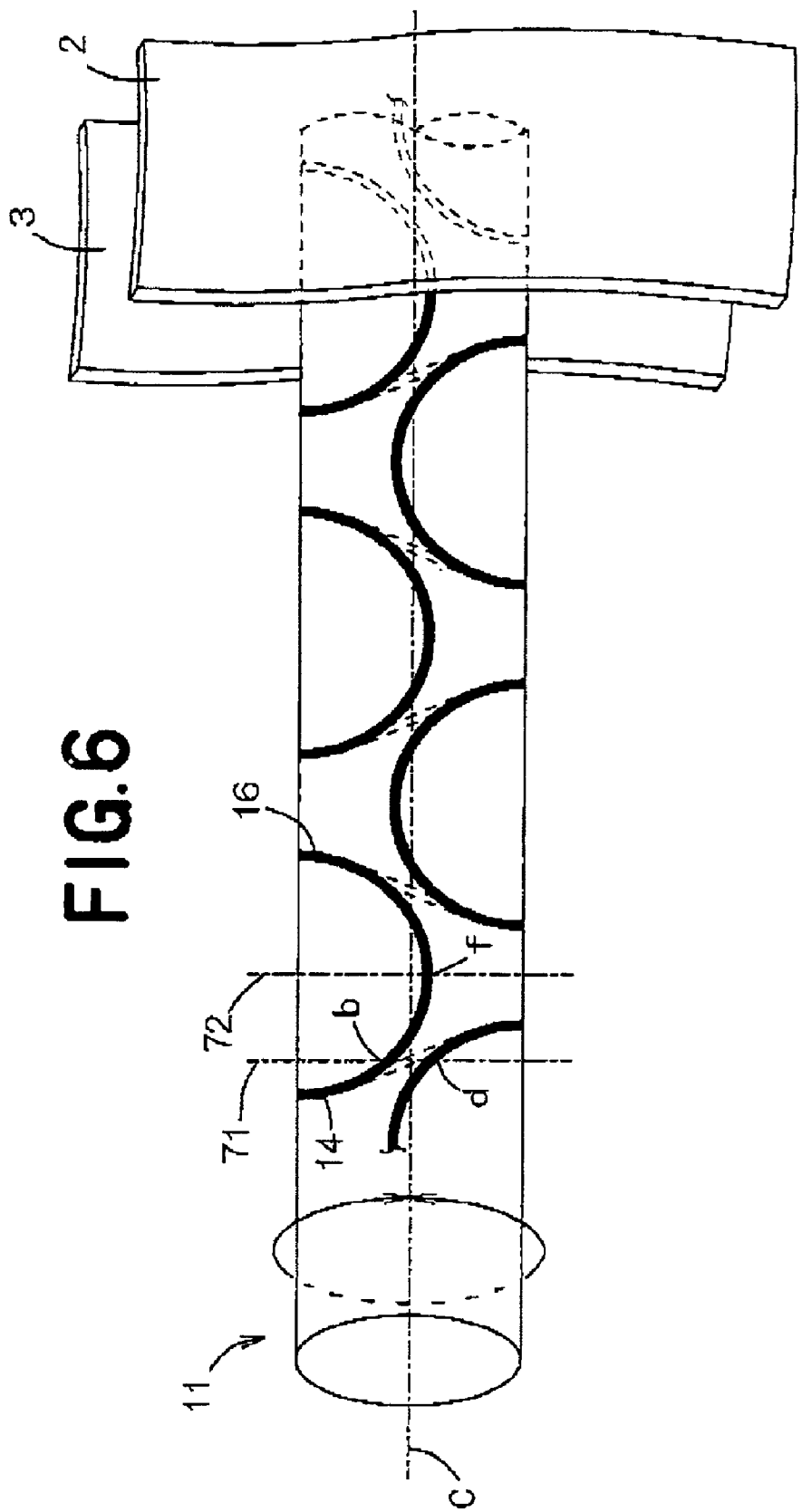
FIG. 6 is a view similar to FIG. 2 but showing further another embodiment of this invention.

FIGS. 6 and 7 are views similar to FIGS. 2, 3 but showing further alternative embodiments of this invention. Referring first to FIG. 7, the curved line 16 drawn by the applied adhesive 14 on the x-y plane meanders in an S- or an inverted s-shape between the values m and –m on the y-axis as it advances along the x-axis. In the case of the elastic member 11 with the curved line 16, the elastic member 11 can be secured to the top- or backsheet 2, 3 depending on the region in the longitudinal direction of the elastic member 11. In a region a, for example, the elastic member 11 can be secured to the top- or backsheet 2, 3 at one of the points b, c, d at which an imaginary line 71 extending in parallel to the y-axis intersects the curved line 16. In a region e, the elastic member 11 can be bonded to the top- or backsheet 2, 3 only at a point f at which an imaginary line 72 intersects the curved line 16. Referring now to FIG. 6, this elastic member 11 can be secured to the topsheet 2 at two points b, d, so the area over which the elastic member 11 is secured to the topsheet 2 can be enlarged in comparison with the case of FIGS. 2 and 3. As will be apparent from these FIGS. 2, 3 and FIGS. 6, 7, it is possible without departing from the scope of this invention to vary the shape of the curved line 16 described on the x-y plane.

If the top- and backsheets 2, 3 of the diaper 1 using the elastic member 11 as illustrated are replaced by elastically stretchabile ones, it is possible to secure the elastic member 11 without extension to such top- and backsheets 2, 3. It is also possible to secure the elastic member 11 without extension to the top- and backsheets 2, 3 having previously formed gathers. As will be obviously understood, the elastic member 11 can be secured to a sheet material forming components other than the top- and backsheets 2, 3. For example, the elastic members 12 associated with each leg-hole can be secured to the diaper 1 in the same manner as in which the elastic member 11 are secured to the diaper 1. With the diaper 1 including elastic members other than the elastic members 11 associated with the waist-hole and the elastic members 12 associated with the leg-hole, such additional elastic member can be also secured to the diaper 1 using the process according to this invention.

According to this invention, the curved line 16 drawn by the applied adhesive 14 around the peripheral surface 13 of the elastic member 11 is preferably a continuous curved line like the illustrated embodiments. However, even if the curved line 16 runs intermittently, such curved line 16 can be considered as being substantially continuous, so far as it is possible for such intermittent curved line 16 to bond the elastic member 11 to the top- and backsheets 2, 3 as effectively as in the case of FIG. 2. For example, even when the elastic member 11 is intermittently coated with the adhesive 14 in a form of many dots or discontinuous short lines, the object of this invention can be achieved to secure the elastic member 11 to the top- and backsheets 2, 3 so far as these dots or lines form substantially a continuous line. While the type of the adhesive 14 is not particularly specified, it is possible to use hot melt adhesive without departing the scope of this invention. On a continuous production line for the diaper 1, a hot melt adhesive may be sprayed in a molten state from right above the elastic member onto it by a spiral spraying process as the elastic member is continuously fed into an adhesive coating step in one horizontal direction to obtain the elastic member 11 coated with the adhesive in the pattern as illustrated in FIG. 2 or 4. The elastic member 11 obtained in this manner may be brought in contact with the top- and backsheets 2, 3 before the adhesive 14 is cured in the subsequent step. There may be contemplated a process where the elastic member 11 is rotated around its longitudinal axis C so that the adhesive 14 may be uniformly distributed over the entire peripheral surface of the elastic member 11. However, the adhesive coating pattern obtained by the process according to this invention makes it unnecessary to rotate the elastic member 11 in such manner and correspondingly simplifies the adhesive coating step.

To implement the process according to this invention, the topsheet 2 of the diaper 1 may be made of a nonwoven fabric or a finely apertured plastic film and the backsheet 3 of the diaper 1 may be made of a plastic film. The core 1 may be formed by fluff pulp or a mixture of fluff pulp and superabsorbent polymer particles. The disposable wearing article to which this invention is applicable includes, in addition to the disposable diaper 1, other various articles such as disposable training pants, a sanitary napkin, a disposable gown used in medical site or the like and disposable trousers. This invention is applicable to these wearing articles for bonding of various elastic members thereto. While each of the elastic members 11 or 12 has been illustrated and described to have the circular cross-section, it is possible to use an elastic member having another appropriate cross-sectional shape such as rectangular or polygonal cross-section without departing from the scope of this invention. A material for the elastic member is not particularly specified, either.

The process according to this invention including, on the production line of the disposable wearing article, the step of bonding the thread-like member having the elastic stretchability in the longitudinal direction to the sheet material is primarily characterized in that the thread-like member is coated with the adhesive in a pattern of substantially continuous line extending around the substantially entire circumference of the elastic member. This unique pattern of coating ensures that the thread-like member is reliably brought in contact with and secured to the sheet material of the wearing article even if the thread-like member is distorted or twisted in the course of continuously feeding these sheet material and thread-like member at high speed.

What is claimed is:

1. A process for making a disposable wearing article comprising a step of securing an elastic member of an elastically stretchable in a longitudinal direction to sheet material of said disposable wearing article using an adhesive, said process further comprising:

providing a disposable wearing article having a topsheet with an inner and outer surface and a backsheet with an inner and outer surface;

providing an elastic member with a first longitudinal line and a second longitudinal line, the second longitudinal line being diametrically opposite the first longitudinal line;

applying an adhesive to said elastic member on a peripheral surface thereof to secure the elastic member between inner surfaces of the topsheet and the backsheet, the adhesive forming a continuous line on the elastic member and defining a cycle path, the cycle path beginning at a point on the first longitudinal line; and traversing the elastic member to cross over the second longitudinal line;

continuing to traverse the elastic member until reaching the first longitudinal line;

crossing over the first longitudinal line and then reversing direction to cross over the first longitudinal line for a second time;

still continuing to traverse the elastic member and crossing over the second longitudinal line;

again crossing over the first longitudinal line and again reversing direction to arrive at a second point on the first longitudinal line and start of a new cycle path; and bringing the elastic member into contact with the inner surfaces of the topsheet and backsheet with the first longitudinal line facing the inner surface of the topsheet and the second longitudinal line facing the inner surface of the backsheet.

2. The method of claim 1, wherein the elastic member is brought into contact with the inner surfaces of the topsheet and backsheet with or without extension.

3. The method of claim 2, wherein the wearing article is one of a disposable diaper, disposable training pants, a sanitary napkin, a disposable gown, and disposable trousers.

* * * * *